United States Patent
Dai et al.

(10) Patent No.: US 11,903,981 B2
(45) Date of Patent: Feb. 20, 2024

(54) **USE OF *ANAEROFUSTIS STERCORIHOMINIS* IN PREVENTING AND/OR TREATING METABOLIC DISEASES**

(71) Applicant: BGI SHENZHEN, Guangdong (CN)

(72) Inventors: Ying Dai, Guangdong (CN); Yuanqiang Zou, Guangdong (CN); Liang Xiao, Guangdong (CN)

(73) Assignee: BGI SHENZHEN, Guangdong (CN)

( * ) Notice: Subject to any disclaimer, the term of this patent is extended or adjusted under 35 U.S.C. 154(b) by 70 days.

(21) Appl. No.: 17/311,176

(22) PCT Filed: Dec. 7, 2018

(86) PCT No.: PCT/CN2018/119910
§ 371 (c)(1),
(2) Date: Jun. 4, 2021

(87) PCT Pub. No.: WO2020/113580
PCT Pub. Date: Jun. 11, 2020

(65) Prior Publication Data
US 2021/0353691 A1    Nov. 18, 2021

(51) Int. Cl.
| | |
|---|---|
| *A61K 35/745* | (2015.01) |
| *A23L 33/135* | (2016.01) |
| *A61P 3/04* | (2006.01) |
| *C12N 1/20* | (2006.01) |
| *A61K 35/747* | (2015.01) |
| *A61K 35/74* | (2015.01) |
| *A61K 35/741* | (2015.01) |
| *A61P 3/00* | (2006.01) |

(52) U.S. Cl.
CPC .......... *A61K 35/745* (2013.01); *A23L 33/135* (2016.08); *A61K 35/74* (2013.01); *A61K 35/741* (2013.01); *A61K 35/747* (2013.01); *A61P 3/00* (2018.01); *A61P 3/04* (2018.01); *C12N 1/205* (2021.05)

(58) Field of Classification Search
CPC .. A61K 35/745; A61K 35/747; A61K 35/741; A61K 35/74; A61K 9/4858; A23L 33/135; A61P 3/04; A61P 3/00; A61P 9/00; C12N 1/205; C12N 1/20; C12R 2001/01
See application file for complete search history.

(56) References Cited

U.S. PATENT DOCUMENTS

| | | | |
|---|---|---|---|
| 11,376,289 B2 * | 7/2022 | Zou | A23L 33/135 |
| 2016/0228476 A1 * | 8/2016 | Cutcliffe | A61P 3/10 |
| 2022/0031770 A1 * | 2/2022 | Dai | C12N 1/20 |

FOREIGN PATENT DOCUMENTS

WO    WO-2019051789 A1 *   3/2019   ............. A61K 35/74

OTHER PUBLICATIONS

Nathalie Esser et. al., Inflammation as a link between obesity, metabolic syndrome and type 2 diabetes, Diabetes Research and Clinical Practice, vol. 105, Issue 2, 2014, pp. 141-150, ISSN 0168-8227, https://doi.org/10.1016/j.diabres.201 (Year: 2014).*
WIPO, International Search Report for PCT/CN2018/119910, dated Aug. 30, 2019.

* cited by examiner

*Primary Examiner* — Paul J Holland
(74) *Attorney, Agent, or Firm* — Hodgson Russ LLP

(57) ABSTRACT

Use of *Anaerofustis stercorihominis* in the prevention and/or treatment of metabolic diseases such as obesity, diabetes, atherosclerosis-related diseases, and cardiovascular diseases.

15 Claims, No Drawings
Specification includes a Sequence Listing.

SEQUENCE LISTING

<160> NUMBER OF SEQ ID NOS: 3

<210> SEQ ID NO 1
<211> LENGTH: 1425
<212> TYPE: DNA
<213> ORGANISM: Anaerofustis stercorihominis

<400> SEQUENCE: 1

| | | | | | |
|---|---|---|---|---|---|
| acgaacgctg | gcggcgtgct | taacacatgc | aagtcgaacg | agaagcttat | aaatgatcct | 60 |
| tcgggtgaag | ctataagcgg | acagtggcga | acgggtgagt | aacgcgtagg | taaccaacct | 120 |
| catgcagggg | gatagcccag | ggaaacttgg | attaaacccg | cataagacca | cagcaccgca | 180 |
| tggtgcaggg | gtaaaaactc | cggtggcatg | agacggacct | gcgtcttatt | aggtagttgg | 240 |
| tgaggtaacg | gctcaccaag | ccaacgatga | gtagccgacc | tgagagggtg | atcggccaca | 300 |
| ttgggactga | gacacggccc | agactcctac | gggaggcagc | agtgggaat  | attgcgcaat | 360 |
| gggggaaacc | ctgacgcagc | aacgccgcgt | gagcgatgaa | ggttttcgga | tcgtaaagct | 420 |
| ctgtctttgg | ggaagataat | gacggtaccc | aaggaggaag | ctccggctaa | ctacgtgcca | 480 |
| gcagccgcgg | taatacgtag | ggagcaagcg | ttgtccggat | tcactgggcg | taaagagcac | 540 |
| gtaggcggtt | aattaagtca | ggtgtgaaag | ttttcggctc | aaccggaaaa | gtgcacttga | 600 |
| aactggataa | cttgagtatc | ggagaggtaa | gcggaattcc | tagtgtagcg | gtgaaatgcg | 660 |
| tagagattag | gaagaacacc | ggtggcgaag | gcggcttact | ggacgataac | tgacgctgag | 720 |
| gtgcgaaagc | gtggggagcg | aacaggatta | gataccctgg | tagtccacgc | cgtaaacgat | 780 |
| gaatactagg | tgttgggta  | actcagtgcc | gcagttaaca | cattaagtat | tccgcctggg | 840 |
| gagtacgctc | gcaagagtga | aactcaaagg | aattgacggg | ggcccgcaca | agcagcggag | 900 |
| catgtggttt | aattcgaagc | aacgcgaaga | accttaccag | gtcttgacat | cccttgaccg | 960 |
| cctaagagat | taggctttcc | ttcgggacaa | ggagacaggt | ggtgcatggt | tgtcgtcagc | 1020 |
| tcgtgtcgtg | agatgttggg | ttaagtcccg | caacgagcgc | aacccttatg | tttagttact | 1080 |
| aacattcagt | tgaggactct | agacagactg | cccttgaaag | agggaggaag | gtgggggacga | 1140 |
| cgtcaaatca | tcatgcccct | tacgacctgg | gctacacacg | tgctacaatg | gtctgtacag | 1200 |
| agggttgcga | agcagtgatg | ctaagctaat | ctcaaaaagc | agatctcagt | tcggattgca | 1260 |
| ggctgcaact | cgcctgcatg | aagtcggagt | tgctagtaat | cgcgaatcag | aatgtcgcgg | 1320 |
| tgaatgcgtt | cccgggcctt | gtacacaccg | cccgtcacac | cacgagagtt | ggtaacaccc | 1380 |
| gaagccagtg | agctaaccat | taggaggcag | ctgtcgaagg | tggga      |            | 1425 |

<210> SEQ ID NO 2
<211> LENGTH: 20
<212> TYPE: DNA
<213> ORGANISM: Artificial Sequence
<220> FEATURE:
<223> OTHER INFORMATION: synthetic sequence

<400> SEQUENCE: 2
agagtttgat catggctcag                                               20

```
<210> SEQ ID NO 3
<211> LENGTH: 22
<212> TYPE: DNA
<213> ORGANISM: Artificial Sequence
<220> FEATURE:
<223> OTHER INFORMATION: synthetic sequence

<400> SEQUENCE: 3
tagggttacc ttgttacgac tt                                        22
```

USE OF *ANAEROFUSTIS STERCORIHOMINIS* IN PREVENTING AND/OR TREATING METABOLIC DISEASES

CROSS-REFERENCE TO RELATED APPLICATIONS

The present application is a national phase entry under 35 USC § 371 of International Application No. PCT/CN2018/119910, filed on Dec. 7, 2018, the entire disclosure of which is incorporated by reference herein.

FIELD

The present disclosure relates to the field of microorganism, in particular to the use of *Anaerofustis stercorihominis* in the prevention and/or treatment of metabolic diseases.

BACKGROUND

Obesity, diabetes, atherosclerosis (AS) and cardiovascular disease all belong to metabolic diseases. Metabolic diseases include lipid metabolism disease and insulin metabolism disease, in which the lipid metabolism disease includes obesity, atherosclerosis related diseases, cardiovascular disease and the like, and the insulin metabolism disease includes diabetes and the like.

Obesity is a chronic disease, which can be caused by several factors and is of a yet unclear origin of disease. The external cause is mainly too much eating and too little activity, resulting in calorie intake more than calorie consumption, thus the increased fat synthesis becomes the material basis for obesity. The internal cause is the disorder of lipid metabolism. Meanwhile, obesity is also an inducer of a series of diseases, such as hypertension, diabetes, coronary heart disease, gallbladder disease, osteoarthritis, sleep apnea, breathing disorder, hysteroma, prostate cancer, breast cancer and colon cancer. According to the report of National Institutes of Health (NIH), currently there are about 97 million Americans being overweight and obese, among them up to about 15.1 million people suffer from obesity-related Type II diabetes, and about 0.2 million people die from obesity-related diseases every year. Further, it is indicated by current studies that the diversity of gut microbes in obese people is remarkably lower than that in normal people.

Diabetes is a disease manifested as abnormally high blood glucose caused by a variety of factors (generally including genetic factors, environmental factors and unhealthy lifestyle), which belongs to a metabolic disorder mainly due to insufficient insulin secretion or insulin dysfunction. The type II diabetes (T2D) is a type of non-insulin dependent diabetes, accounting for 90% of all diabetes patients. A large number of studies have shown that the onset of type II diabetes mainly resulted from insulin resistance and low-level inflammation reaction is closely related to the disorder of intestinal flora which is tightly associated to the regulation of energy balance and inflammatory response in a host.

Atherosclerosis (AS) is the main cause of coronary heart disease, cerebral infarction and peripheral vascular disease, in which lipid metabolism abnormity is the basis of atherosclerotic lesions. The atherosclerosis is characterized by arteries involved lesions, which are initiated from intima, generally occurring the accumulation of lipids and complex sugars, bleeding and thrombosis, followed by fibrous tissue hyperplasia and calcium deposition, and then gradual metamorphosis and calcification of middle layer of artery which results in thickening and hardening of arterial wall and narrowing of vascular cavity. Once the lesions, always involving in the large and medium-sized muscular arteries, develop enough to block the arterial cavity, the tissues or organs supplied by the arteries will be ischemic or necrotic. The atherosclerosis which is named after the yellow atheromatous appearance of lipid accumulated in the intima of arteries, is caused by combined factors, with complicated pathogenesis. Among them, the main risk factors for atherosclerosis include hypertension, hyperlipidemia and heavy smoking, as well as diabetes, obesity, genetic factors and the like.

Atherosclerotic cardiovascular disease (ACVD) is the number one killer in developed countries and is increasingly common in developing countries. In recent years, with the rapidly developed economy in our country and significantly improved living standards of people, lifestyles are undergoing profound changes, including accelerated pace of work and life, increased dietary calories and decreased physical activities. Such unhealthy lifestyles result in significant increase on risk factors of cardiovascular diseases (such as obesity and the like), thereby further leading to the rapid increase on incidence of cerebrovascular diseases. For example, diseases such as stroke, myocardial infarction and the like can lead to severe disability, reduced life quality and heavy medical burden. Cardio-cerebrovascular diseases have become the major public health problem in our country in this century due to high morbidity, mortality and disability.

ACVD mainly includes coronary heart disease (CHD), stroke and peripheral arterial diseases. The etiology of ACVD is multifaceted, and many of related factors are associated with lifestyle including smoking, atherosclerotic diet, overweight or obesity, sedentariness, lack of physical activity and the like. Coronary heart disease is a heart disease caused by myocardial ischemia and hypoxia by coronary atherosclerosis, also known as ischemic heart disease. The pathological pathogenesis of coronary heart disease is mainly the increased blood lipids due to lipid metabolism disorder, lipid deposition and infiltration in the inner wall of blood vessel, formation of vascular endothelial foam cells, and chronic inflammatory reactions in blood vessel wall that damage the function and morphology of coronary vascular endothelial cells, formation of vascular endothelial atherosclerotic plaque, further plaque rupture, thrombosis, vascular stenosis or occlusion resulting in coronary blood circulation disorder, myocardial ischemia, damaged myocardial cells, and cardiac insufficiency caused. With the improvement of living standards, the incidence and mortality of coronary heart disease in our country have increased yearly and exhibit a trend of getting younger.

The existing means for treating obesity includes dieting, exercise, behavior therapy, drug therapy and rehabilitation surgery. The hypoglycemic drugs for diabetes include sulfonylureas, α-glucosidase inhibitors and biguanides. Coronary heart disease is treated mainly through drugs, intervention or surgery.

Treatment of obesity includes diet-exercise therapy, meaning eating low-calorie and low-fat foods and doing aerobic exercise. However, it is generally considered that this treatment may do not bring significant effect to the general public for the requirement of long-term persistence; the removal of body fat may achieve an immediate result, but having limiting factors such as the risk of surgery, difficulty in lasting the fat removal effect, high cost and the like. In addition, application of drugs may cause local or systemic allergies or immune resistance to drugs. For example, the hypoglycemic drugs used to treat diabetes include sulfonylureas, α-glucosidase inhibitors and biguanides. Among them, sulfonylureas mainly promote insulin secretion, but can cause severe liver and kidney damage, thus are not suitable for allergic physique; α-glucosidase inhibitors inhibit the hydrolysis of carbohydrates mainly by inhibiting the activity of α-amylase and α-glucosidase in the intestine, thereby realizing the purpose of lowering blood glucose after meals, but it is easy to cause adverse reactions such as bloating, diarrhea or the like; biguanides are capable of decreasing blood glucose by regulating the blood glucose transport, such as delaying glucose absorption, promoting glucose decomposition, inhibiting the generation of liver glucose, and increasing the amount of glucose transfer protein, but also cause some side effects, easily causing gastrointestinal discomfort, diarrhea, vomiting, skin rash, and prone to inactivation in a long-term use. Drug treatment for coronary heart disease may cause side effects such as headaches, nausea and vomiting, skin allergies and the like; interventional therapy, despite having a great progress, has the problems of a high probability of recurrence, and restenosis which has been limiting the development of stents, in which the existing drug stents though capable of preventing recurrence, may lead to the formation of thrombosis, even incur sudden death in severe cases; and surgical treatment is also faced with disadvantages of large surgical trauma, a high cost, a high risk for elderly and weak patients as well as patients with severely function impairment on vital organs.

Therefore, there is an urgent need in the art to develop a new and non-toxic and side effect composition for the prevention and/or treatment of metabolic diseases such as obesity, diabetes, atherosclerosis-related diseases and cardiovascular disease, especially a pharmaceutical composition.

SUMMARY

The present disclosure in embodiments provides a new and non-toxic and low side effect composition for the prevention and/or treatment of metabolic diseases.

In a first aspect, provided in embodiments is use of *Anaerofustis stercorihominis* in the preparation of a composition for preventing and/or treating metabolic diseases.

In a preferred embodiment, the *Anaerofustis stercorihominis* has a sequence of 16s rDNA as shown in SEQ ID NO: 1 or with 99% or above sequence similarity to SEQ ID NO: 1.

In a preferred embodiment, the *Anaerofustis stercorihominis* is *Anaerofustis stercorihominis* AM25-6 with a deposit number of GDMCC 60087, *Anaerofustis stercorihominis* DSM 17244 or *Anaerofustis stercorihominis* DSM 28733, or a combination thereof.

In a preferred embodiment, the *Anaerofustis stercorihominis* is derived from intestine, animal faeces, a fermentation tank and/or an anaerobic reactor.

In a preferred embodiment, the *Anaerofustis stercorihominis* is derived from human or non-human mammals.

In a preferred embodiment, the non-human mammal includes rodents such as mice and rats, and primates such as monkey.

In a preferred embodiment, the metabolic disease comprises a lipid metabolism disease, and/or an insulin metabolism disease.

In a preferred embodiment, the metabolic disease is selected from the group consisting of obesity, diabetes, atherosclerosis-related diseases, cardiovascular disease, or a combination thereof.

In a preferred embodiment, the atherosclerosis-related diseases are selected from the group consisting of coronary heart disease, coronary artery disease (CAD), atherosclerotic heart disease, atherosclerotic cardiovascular disease, ischemic heart disease or a combination thereof In a preferred embodiment, the cardiovascular disease is selected from the group consisting of acute coronary syndrome, angina pectoris, arterial sclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemia, dyslipoproteinemia, endothelial dysfunction, familial hypercholesterolemia, familial combined hyperlipidemia, hypo-α lipoproteinemia, hypertriglyceridemia, hyper-β lipoproteinemia, hypercholesterolemia, hypertension, hyperlipidemia, intermittent claudication, ischemia, ischemia reperfusion injury, ischemia heart disease, myocardial ischemia, metabolic syndrome, multiple cerebral infarction dementia, myocardial infarction, obesity, peripheral vascular disease, reperfusion injury, restenosis, renal atherosclerosis, rheumatic heart disease, stroke, thrombosis disorder, transient ischemic attacks, and lipoprotein abnormalities related to Alzheimer's disease, obesity, diabetes, general X, impotence, multiple sclerosis, Parkinson's disease, inflammatory disease, or combinations thereof.

In a preferred embodiment, the composition comprises: (a) a safe and effective amount of *Anaerofustis stercorihominis* and/or its metabolites, and (b) a food acceptable or pharmaceutically acceptable carrier.

In a preferred embodiment, the composition further comprises a growth factor, preferably a milk growth factor.

In a preferred embodiment, the composition is selected from the group consisting of a food composition, a health care composition, a pharmaceutical composition, a beverage composition, a feed composition or a combination thereof.

In a preferred embodiment, the composition is an oral preparation.

In a preferred embodiment, the composition is a liquid preparation, a solid preparation or a semi-solid preparation.

In a preferred embodiment, the dosage form of the composition is selected from the group consisting of powder, pulvis, tablet, sugar coating agent, capsule, granule, suspension, solution, syrup, drop, sublingual tablet or a combination thereof.

In a preferred embodiment, the food composition includes an emulsion product, a solution product, a powder product or a suspension product.

In a preferred embodiment, the food composition includes dairy, milk powder or emulsion.

In a preferred embodiment, the liquid preparation is selected from the group consisting of a solution product or a suspension product.

In a preferred embodiment, the composition comprises $1 \times 10^{-1}$ to $1 \times 10^{20}$ cfu/mL or cfu/g of *Anaerofustis stercorihominis*, preferably $1 \times 10^{4}$ to $1 \times 10^{15}$ cfu/mL or cfu/g of *Anaerofustis stercorihominis*.

In a preferred embodiment, the composition comprises 0.0001 to 99 wt %, preferably 0.1 to 90 wt % of *Anaerofustis stercorihominis* and/or its metabolites, based on the total weight of the composition.

In a preferred embodiment, the composition is in a unit dosage form, i.e., one tablet, one capsule or one vial, and the composition in each unit dosage form is of a mass of 0.05 g to 5 g, preferably 0.1 g to 1 g.

In a preferred embodiment, the composition further comprises probiotics and/or prebiotics.

In a preferred embodiment, the composition is a probiotic agent, a microecological preparation or a pharmaceutical preparation.

In a preferred embodiment, the probiotic agent is a probiotic milk product or a probiotic tablet.

In a preferred embodiment, the probiotics are selected from the group consisting of Lactic acid bacteria, *Bifidobacteria, Lactobacillus acidophilus* or a combination thereof.

In a preferred embodiment, the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

In a preferred embodiment, the composition further contains a substance capable of maintaining the viability of *Anaerofustis stercorihominis*, such as a protective agent.

In a preferred embodiment, the substance capable of maintaining the viability of *Anaerofustis stercorihominis* such as a protective agent is selected from the group consisting of cysteine, glutathione, butyl hydroxyanisole, dibutylmethyltoluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof, especially Vitamin C.

In a preferred embodiment, the substance capable of maintaining the viability of *Anaerofustis stercorihominis* such as a protective agent is of a weight ratio of 0.1% to 2%, preferably 0.5% to 1.5%, more preferably 0.5% to 1.0%, based on the total weight of the composition.

In a preferred embodiment, the substance capable of maintaining the viability of *Anaerofustis stercorihominis* such as a protective agent is of an amount of 1 mg to 20 mg, preferably 5 mg to 15 mg, more preferably 5 mg to 10 mg, based on 1 g of the composition.

In a second aspect, provided in embodiments is use of *Anaerofustis stercorihominis* in the preparation of a composition for exhibiting one or more activities from the group consisting of:

(i) reducing a blood glucose level in mammals;
(ii) ameliorating glucose intolerance in mammals;
(iii) ameliorating myocardial ischemia in mammals;
(iv) reducing a blood lipid level in mammals;
(v) reducing body weight of mammals; and
(vi) ameliorating vasculopathy in mammals.

In a preferred embodiment, the mammals include human or non-human mammals.

In a preferred embodiment, the non-human mammal includes rodents such as mice and rats, and primates such as monkey.

In a preferred embodiment, ameliorating vasculopathy in mammals includes amelioration of one or more indicators selected from the group consisting of blood viscosity, blood rheology, blood pressure, blood lipids (such as triglyceride, total cholesterol, high-density lipoprotein, low-density lipoprotein) and ST segment of electrocardiogram.

In a preferred embodiment, reducing a blood lipid level in mammals includes reducing total cholesterol level, triglyceride level, low-density lipoprotein level and/or blood viscosity level in blood.

In a preferred embodiment, reducing body weight of mammals indicates that the body weight of mammal in an experimental group is reduced by 10% or above, preferably 15% to 20% compared to that of mammal in a model group.

In a preferred embodiment, ameliorating myocardial ischemia in mammals includes reducing ST segment displacement of myocardial ischemia in the mammal.

In a third aspect, provided in embodiments is *Anaerofustis stercorihominis* or a composition comprising *Anaerofustis stercorihominis* for use in the prevention and/or treatment of metabolic diseases.

In a preferred embodiment, the *Anaerofustis stercorihominis* has a sequence of 16s rDNA as shown in SEQ ID NO: 1 or with 99% or above sequence similarity to SEQ ID NO: 1.

In a preferred embodiment, the *Anaerofustis stercorihominis* is *Anaerofustis stercorihominis* AM25-6 with a deposit number of GDMCC 60087, *Anaerofustis stercorihominis* DSM 17244 or *Anaerofustis stercorihominis* DSM 28733, or a combination thereof.

In a preferred embodiment, the *Anaerofustis stercorihominis* is derived from intestine, animal faeces, a fermentation tank and/or an anaerobic reactor.

In a preferred embodiment, the *Anaerofustis stercorihominis* is derived from human or non-human mammals.

In a preferred embodiment, the non-human mammal includes rodents such as mice and rats, and primates such as monkey.

In a preferred embodiment, the metabolic disease comprises a lipid metabolism disease, and/or an insulin metabolism disease.

In a preferred embodiment, the metabolic disease is selected from the group consisting of obesity, diabetes, atherosclerosis-related diseases, cardiovascular disease, or a combination thereof.

In a preferred embodiment, the composition comprises: (a) a safe and effective amount of *Anaerofustis stercorihominis* and/or its metabolites, and (b) a food acceptable or pharmaceutically acceptable carrier.

In a preferred embodiment, the composition further comprises a growth factor, preferably a milk growth factor.

In a preferred embodiment, the composition is selected from the group consisting of a food composition, a health care composition, a pharmaceutical composition, a beverage composition, a feed composition or a combination thereof.

In a preferred embodiment, the composition is an oral preparation.

In a preferred embodiment, the composition is a liquid preparation, a solid preparation or a semi-solid preparation.

In a preferred embodiment, the dosage form of the composition is selected from the group consisting of powder, pulvis, tablet, sugar coating agent, capsule, granule, suspension, solution, syrup, drop, sublingual tablet or a combination thereof.

In a preferred embodiment, the food composition includes an emulsion product, a solution product, a powder product or a suspension product.

In a preferred embodiment, the food composition includes dairy, milk powder or emulsion.

In a preferred embodiment, the liquid preparation is selected from the group consisting of a solution product or a suspension product.

In a preferred embodiment, the composition comprises $1 \times 10^{-1}$ to $1 \times 10^{20}$ cfu/mL or cfu/g of *Anaerofustis stercorihominis*, preferably $1 \times 10^4$ to $1 \times 10^{15}$ cfu/mL or cfu/g of *Anaerofustis stercorihominis*.

In a preferred embodiment, the composition comprises 0.0001 to 99 wt %, preferably 0.1 to 90 wt % of *Anaerofustis stercorihominis* and/or its metabolites, based on the total weight of the composition.

In a preferred embodiment, the composition is in a unit dosage form, i.e., one tablet, one capsule or one vial, and the composition in each unit dosage form is of a mass of 0.05 g to 5 g, preferably 0.1 g to 1 g.

In a preferred embodiment, the composition further comprises probiotics and/or prebiotics.

In a preferred embodiment, the composition is a probiotic agent, a microecological preparation or a pharmaceutical preparation.

In a preferred embodiment, the probiotic agent is a probiotic milk product or a probiotic tablet.

In a preferred embodiment, the probiotics are selected from the group consisting of Lactic acid bacteria, *Bifidobacteria*, *Lactobacillus acidophilus* or a combination thereof.

In a preferred embodiment, the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

In a preferred embodiment, the *Anaerofustis stercorihominis* and/or its metabolites are combined with prebiotics, optionally also combined with probiotics, which can be made into forms such as a tableting candy, a capsule or the like, so as to further change the type of probiotic agent, thereby maintaining the activity of *Anaerofustis stercorihominis* and achieving the corresponding preventive and/or therapeutic efficacy.

In a preferred embodiment, the composition further contains a substance capable of maintaining the viability of *Anaerofustis stercorihominis*, such as a protective agent.

In a preferred embodiment, the substance capable of maintaining the viability of *Anaerofustis stercorihominis* such as a protective agent is selected from the group consisting of cysteine, glutathione, butyl hydroxyanisole, dibutylmethyltoluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof.

In a preferred embodiment, the substance capable of maintaining the viability of *Anaerofustis stercorihominis* such as a protective agent is of a weight ratio of 0.1% to 2%, preferably 0.5% to 1.5%, more preferably 0.5% to 1.0%, based on the total weight of the composition.

In a preferred embodiment, the substance capable of maintaining the viability of *Anaerofustis stercorihominis* such as a protective agent is of an amount of 1 mg to 20 mg, preferably 5 mg to 15 mg, more preferably 5 mg to 10 mg, based on 1 g of the composition.

In a fourth aspect, provided in embodiments is *Anaerofustis stercorihominis* or a composition comprising *Anaerofustis stercorihominis* for use in exhibiting one or more activities from the group consisting of:
(i) reducing a blood glucose level in mammals;
(ii) ameliorating glucose intolerance in mammals;
(iii) ameliorating myocardial ischemia in mammals;
(iv) reducing a blood lipid level in mammals;
(v) reducing body weight of mammals; and
(vi) ameliorating vasculopathy in mammals.

In a fifth aspect, provided in embodiments is a method for preparing the composition of the third aspect or the fourth aspect, comprising:
mixing (a) an *Anaerofustis stercorihominis* and/or its metabolites with (b) a food acceptable or pharmaceutically acceptable carrier to form the composition of the third aspect or the fourth aspect.

In a preferred embodiment, the method further comprises a step of mixing with probiotics and/or prebiotics.

In a preferred embodiment, the method further comprises a step of mixing with a substance capable of maintaining the vitality of *Anaerofustis stercorihominis*.

In a sixth aspect, provided in embodiments is a method for preventing and/or treating metabolic diseases, comprising:
administering an *Anaerofustis stercorihominis* or a composition comprising the *Anaerofustis stercorihominis* to a subject in need to prevent and/or treat the metabolic diseases.

In a preferred embodiment, the *Anaerofustis stercorihominis* has a sequence of 16s rDNA as shown in SEQ ID NO: 1 or with 99% or above sequence similarity to SEQ ID NO: 1.

In a preferred embodiment, the *Anaerofustis stercorihominis* is *Anaerofustis stercorihominis* AM25-6 with a deposit number of GDMCC 60087, *Anaerofustis stercorihominis* DSM 17244 or *Anaerofustis stercorihominis* DSM 28733, or a combination thereof.

In a preferred embodiment, the composition is an oral preparation.

In a preferred embodiment, the administration dosage is 0.01 to 5 g/50 kg body weight per day, preferably 0.1 to 2 g/50 kg body weight per day.

In a preferred embodiment, the subject includes human or non-human mammals.

In a preferred embodiment, the non-human mammal includes rodents such as mice and rats, and primates such as monkey.

In a preferred embodiment, the method is non-diagnostic or non-therapeutic.

In a preferred embodiment, the metabolic disease comprises a lipid metabolism disease, and/or an insulin metabolism disease.

In a preferred embodiment, the metabolic disease is selected from the group consisting of obesity, diabetes, atherosclerosis-related diseases, cardiovascular disease, or a combination thereof.

In a preferred embodiment, the composition comprises: (a) a safe and effective amount of *Anaerofustis stercorihominis* and/or its metabolites, and (b) a food acceptable or pharmaceutically acceptable carrier.

In a preferred embodiment, the composition comprises $1 \times 10^{-1}$ to $1 \times 10^{20}$ cfu/mL or cfu/g of *Anaerofustis stercorihominis*, preferably $1 \times 10^{4}$ to $1 \times 10^{15}$ cfu/mL or cfu/g of *Anaerofustis stercorihominis*, based on the total volume or total weight of the composition.

In a preferred embodiment, the composition further comprises probiotics and/or prebiotics.

In a preferred embodiment, the composition further comprises a substance capable of maintaining the vitality of *Anaerofustis stercorihominis*.

In a preferred embodiment, the composition is selected from the group consisting of a food composition, a health care composition, a pharmaceutical composition, a beverage composition, a feed composition, or a combination thereof.

In a seventh aspect, provided in embodiments is a method for achieving one or more activities from the group consisting of:
(i) reducing a blood glucose level in mammals;
(ii) ameliorating glucose intolerance in mammals;
(iii) ameliorating myocardial ischemia in mammals;
(iv) reducing a blood lipid level in mammals;
(v) reducing body weight of mammals; and
(vi) ameliorating vasculopathy in mammals, by administering an *Anaerofustis stercorihominis* or a composition comprising the *Anaerofustis stercorihominis* to a subject in need.

*Anaerofustis stercorihominis* in the present disclosure shows significant efficacy on type II diabetes, capable of ameliorating symptoms such as high blood glucose and the like, and also capable of remarkably relieving the glucose intolerance of diabetes patients. *Anaerofustis stercorihominis* in the present disclosure can also effectively reduce the serum cholesterol content, thus avoiding atherosclerosis and alleviating coronary heart disease. Meanwhile, it is also found that *Anaerofustis stercorihominis* can effectively alleviate myocardial ischemic disease, such as reducing the ST-segment displacement of myocardial ischemia in mammals thus ameliorating vasculopathy through research of effect of *Anaerofustis stercorihominis* on experimental myocardial ischemia in rats. Therefore, the *Anaerofustis stercorihominis* of the present disclosure is useful in the preparation of a composition for preventing and/or treating metabolic diseases.

DETAILED DESCRIPTION

The present disclosure is further described in detail through specific embodiments in the below. In the following embodiments, many details are described in order to enable the present disclosure to be better understood. However, those skilled persons in the art can easily appreciated that some of the features can be omitted under different circumstances or can be replaced by other materials or methods.

Additionally, the features, operations or features described in the specification can be combined in any appropriate manner to constitute various implementations. Meanwhile, the steps or actions described in the method can also be sequentially exchanged or adjusted in a manner obvious to those skilled in the art. Therefore, the various sequences in the specification are only for clearly describing a certain embodiment and do not mean a necessary sequence, unless otherwise stated that a certain sequence is required to be followed.

After extensive and in-depth research and experiments, inventors of the present application unexpectedly discovered that *Anaerofustis stercorihominis* is capable of preventing and/or treating metabolic diseases (such as obesity, diabetes, atherosclerosis-related diseases, cardiovascular disease). Through administration of an active composition containing *Anaerofustis stercorihominis* to experimental subjects, it is discovered that the composition can significantly control the weight gain rate of subjects (such as mice), effectively slow down the weight gain of subjects (such as mice), effectively reduce blood glucose, effectively ameliorate glucose intolerance of diabetic subjects (such as mice), and effectively control the levels of TC, TG, LDLC in blood and blood viscosity, thereby reducing blood lipids and the indicators related to atherosclerosis-related diseases, thus having an excellent relieving and protecting effect on myocardial ischemia. Therefore, it is shown that *Anaerofustis stercorihominis* can effectively alleviate metabolic diseases (such as obesity, diabetes, atherosclerosis-related diseases, cardiovascular disease) or the like. On this basis, the present application is completed by the inventors.

As used herein, the terms "comprising", "including" or "containing" mean that various ingredients can be applied together in the mixture or composition of the present disclosure. Therefore, the terms "mainly consisting of" and "consisting of" are included in the scope of terms "comprising", "including" or "containing".

As used herein, the term "growth factor" includes a milk growth factor, specifically including nutrients of vitamins, purines, pyrimidines or a combination thereof. In which, the vitamins include but are not limited to Vitamin C, Vitamin E, Vitamin A, Vitamin A precursor, Vitamin $B_6$, Vitamin $D_3$, Vitamin K, folic acid or a combination thereof; the purines include but are not limited to purine nucleosides, which include 5'-phosphate esters of purine nucleosides; the 5'-phosphate esters of purine nucleosides are selected from the group consisting of inosinic acid (inosine-5'-phosphate ester; IMP), guanylic acid (guanosine-5'-phosphate ester; GMP), xanthylic acid (xanthine-5'-phosphate ester; XMP), adenylic acid (adenosine-5'-phosphate ester; AMP) or a combination thereof; the pyrimidines include all substances containing a pyrimidine structure.

As used herein, the terms "reducing the body weight of mammals", "controlling the weight gain of mammals" and "slowing down the weight gain of mammals" can be used interchangeably and refer to the treatment of weight gain symptoms caused by obesity.

As used herein, the term "ameliorating vasculopathy in mammals" refers to the treatment of symptoms of vasculopathy caused by atherosclerosis. In the present disclosure, ameliorating vasculopathy in mammals includes amelioration of one or more indicators selected from the group consisting of: blood viscosity, blood rheology, blood lipids (mainly triglyceride, total cholesterol, high-density lipoprotein and low-density lipoprotein), ST segment of electrocardiogram.

As used herein, the term "ST-segment displacement of myocardial ischemia" refers to that myocardial ischemia can be diagnosed by electrocardiography, mainly manifested as depression or elevation of ST-segment.

*Anaerofustis stercorihominis* and its Application

As used herein, the terms "strain *Anaerofustis stercorihominis*", "*Anaerofustis stercorihominis*" and "*Anaerofustis stercorihominis* of the present disclosure" can be used interchangeably. In a preferred embodiment, the strain is *Anaerofustis stercorihominis* AM25-6 with a deposit number of GDMCC 60087, which is isolated from human feces, preferably a healthy male. The physiological characteristics of *Anaerofustis stercorihominis* is described as follows: the *Anaerofustis stercorihominis* AM25-6 is isolated by using peptone yeast extract glucose (PYG) medium in an anaerobic condition at 37° C. The colony of *Anaerofustis stercorihominis* AM25-6 after culturing for 2 days in PYG medium is light yellow, needle-shaped and small size, with a diameter of about 0.5 mm. The mycelium under microscope is short rod-shaped, Gram-positive, and does not produce spores and flagella. *Anaerofustis stercorihominis* AM25-6 is detected to be negative to both catalase and oxidase. *Anaerofustis stercorihominis* AM25-6 can produce several carbohydrates after fermentation, including glucose, mannitol, lactose, sucrose, maltose, salicyl alcohol, xylose, mannose, melezitose, raffinose, sorbitol, rhamnose and trehalose; can mainly produce acetic acid, butyric acid, isovaleric acid, benzoic acid and lactic acid; and can also produce a small amount of isobutyric acid, valeric acid, 3-methyl butyric acid, succinic acid, adipic acid and citric acid. Moreover, the *Anaerofustis stercorihominis* AM25-6 of the present disclosure is sensitive to all of the 20 common antibiotics in Table 2.

The present disclosure provides the application of *Anaerofustis stercorihominis* in the treatment and/or prevention of metabolic diseases (such as obesity, diabetes, atherosclerosis-related diseases, cardiovascular disease). Subjects (such as mice) having the similar body weight, age and the like are fed with high-fat diet and injected with streptase urea (STZ) to induce a type II diabetes (T2D) model. After intragastric administration of *Anaerofustis stercorihominis*, the subjects are observed on body weight, blood glucose and glucose tolerance to reflect the therapeutic effect of *Anaerofustis stercorihominis* on T2D. Through high-fat feeding subjects (such as mice) with the similar body weight, age and the like, the effect of *Anaerofustis stercorihominis* on serum cholesterol content under high-fat feeding conditions is investigated, so as to indirectly reflect the efficacy of *Anaerofustis stercorihominis* on atherosclerosis-related diseases. Meanwhile, the research found that *Anaerofustis stercorihominis* can effectively ameliorate myocardial ischemic disease, such as decreasing the ST-segment displacement of myocardial ischemia in mammals, thus relieving vascular disease, based on the effects on experimental myocardial ischemia in rats. It is found through the experimental results that *Anaerofustis stercorihominis* of the present disclosure can ameliorate a series of indicators related to metabolic diseases (such as obesity, diabetes, atherosclerosis-related diseases, cardiovascular disease), for example, significantly controlling the weight gain rate of subjects (such as mice), effectively slowing down the weight gain of subjects (such as mice), effectively reducing blood glucose level, effectively ameliorating glucose intolerance in subjects (such as mice) with diabetes, and effectively controlling the levels of TC, TG, LDLC in blood and blood viscosity, indicating the ability of *Anaerofustis stercorihominis* on reduction of blood lipids and indicators related to atherosclerosis-related diseases. According to another preferred embodiment of the present invention, SD rats are used as test rats and are treated with pituitrin. Compared to the untreated control group (model group), the pituitrin-treated test rats which are further treated with strain *Anaerofustis stercorihominis* exhibited significantly reduced cardiovascular disease-related indicators (such as ST segment displacement of myocardial ischemia), indicating that the *Anaerofustis stercorihominis* has excellent relieving and protecting effects on myocardial ischemia. Therefore, *Anaerofustis stercorihominis* of the present disclosure can effectively alleviate metabolic diseases (such as obesity, diabetes, atherosclerosis-related diseases, cardiovascular disease) and the like.

Composition and its Application

The *Anaerofustis stercorihominis* of the present disclosure can be useful in the preparation of a composition for treating and/or preventing metabolic diseases. Preferably, the composition includes a food composition, a health care composition, a pharmaceutical composition, a beverage composition or a feed composition. More preferably, the composition is a pharmaceutical composition. The composition contains an effective amount of *Anaerofustis stercorihominis*. In a preferred embodiment, the composition further contains a growth factor, such as a milk growth factor. In a preferred embodiment, the composition further contains probiotics selected from the group consisting of Lactic acid bacteria, *Bifidobacteria*, *Lactobacillus acidophilus* or a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Anaerofustis stercorihominis* (such as a protective agent), which includes cysteine, glutathione, butyl hydroxyanisole, dibutylmethyltoluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof. The substance capable of maintaining the viability of *Anaerofustis stercorihominis* (such as a protective agent) is of a weight ratio of 0.1% to 2%, preferably 0.5% to 1.5%, more preferably 0.5% to 1.0%, based on the total weight of the composition. In a preferred embodiment, the composition is a liquid preparation, a solid preparation or a semi-solid preparation. In a preferred embodiment, the liquid preparation is selected from the group consisting of a solution product or a suspension product. In a preferred embodiment, the dosage form of the composition is selected from the group consisting of powder, pulvis, tablet, sugar coating agent, capsule, granule, suspension, solution, syrup, drop, sublingual tablet or a combination thereof.

The composition of the present disclosure may be administered in any form of oral solution, tablet, injection, orally disintegrating tablet, lyophilized powder or capsule, preferably in the dosage form of enteric agent (such as capsule). In the present disclosure, the excipient, pharmaceutically acceptable vehicle and carrier used in the present disclosure are mainly selected depending on the property suitable for the bacteria or metabolites thereof and the specific administration means required, which is beneficial to the smooth passage of the bacteria or metabolites thereof through stomach thus absorbed by the administered subject, unless especially indicated. These substances can be selected according to the administration routes.

The composition of the present disclosure may further contain any additional excipients commonly used in a pharmaceutical preparation, for example, for stabilization of the composition itself, or allowing to be easily dispersed or imparting a suitable taste. Among the excipients, suitable examples are inulin, fructose, starch, xylooligosaccharide, silicon dioxide, buffering agent and flavoring agent.

Lactose, maltodextrin, glucose, sucrose, sorbitol, mannose, starch, arabic gum, calcium phosphate, alginate, gelatin, calcium silicate, fine crystalline cellulose, polyvinylpyrrolidone (PVP), cellulose, water, syrup, methyl cellulose, methyl hydroxybenzoate, propyl hydroxybenzoate, talc, magnesium stearate, mineral oil and the like can be all used as carriers, excipients, diluents and the like of the pharmaceutical composition of the present disclosure.

Further, the pharmaceutical composition of the present disclosure may further contain lubricant, wetting agent, emulsifier, suspension stabilizer, preservative, sweetening agent, flavor and the like. The pharmaceutical composition of the present disclosure can be produced in an enteric coating preparation via a variety of well-known methods, so that the active component of the pharmaceutical composition (i.e., the microorganism) can pass through stomach smoothly without destroyed by gastric acid.

Further, the microorganism of the present disclosure may be used in the form of capsule prepared by conventional methods. For example, standard excipients and lyophilized microorganism of the present disclosure are mixed to obtain pills which are subsequently dispensed into gelatin capsules. In addition, the microorganism of the present disclosure and pharmaceutically acceptable excipients (such as liquid gum, cellulose, silicate, mineral oil and the like) can be mixed and prepared into a suspension liquid or a dispersion liquid, and such a suspension or dispersion liquid can be filled into soft gelatin capsules.

The pharmaceutical composition of the present disclosure can be prepared into enteric coating tablets for oral use. The term "enteric coating" in the present disclosure includes all coatings that are allowed for conventional drugs. These coatings are not degraded by gastric acid, however, can be completely broken down in small intestine and then quickly release the microorganism of the present disclosure. The enteric coating of the present disclosure can be maintained in an HCl solution suitable for gastric acid synthesis (such as pH=1) at 36° C. to 38° C. for more than 2 hours, preferably broken down in a buffer solution suitable for intestinal fluid synthesis (such as pH=7.0) within one hour.

The enteric coating of the present disclosure is coated in an amount of about 16 to 30 mg per tablet, preferably 16 to 25 mg per tablet, and more preferably 16 to 20 mg per tablet. The thickness of the enteric coating in the present disclosure is 5 to 100 μm, ideally 20 to 80 μm. The components of enteric coating are selected from conventional polymers which are known in public.

The preferred enteric coating of the present disclosure is prepared by a copolymer of cellulose acetate phthalate polymer (or cellulose acetate trimellitate polymer) and methacrylic acid, for example, a copolymer of methacrylic acid (in an amount of 40% or above) and methylcellulose hydroxypropyl phthalate or its ester derivatives.

The cellulose acetate phthalate used in the enteric coating of the present disclosure has a viscosity of about 45 to 90 cp, an acetyl content of 17 to 26%, and a phthalic acid content of 30 to 40%. The cellulose acetate trimellitate used in the enteric coating has a viscosity of about 5 to 21 cp, and an acetyl content of 17 to 26%. Cellulose acetate trimellitate, produced by Eastman Kodak Company, can be used as the enteric coating material in the present disclosure.

The hydroxypropyl methylcellulose phthalate used in the enteric coating of the present disclosure generally has a molecular weight of 20,000 to 130,000 Daltons (ideally 80,000 to 100,000 Daltons), a hydroxypropyl content of 5 to 10%, a methoxyl content of 18 to 24% and a phthaloyl content of 21 to 35%.

The hydroxypropyl methylcellulose phthalate used in the enteric coating of the present disclosure is HP50, produced by Shin-Etsu Chemical Co. Ltd. of Japan. HP50 contains 6 to 10% of hydroxypropyl, 20 to 24% of methoxy and 21 to 27% of propyl, with a molecular weight of 84,000 Daltons. Another enteric coating material is HP55, which contains 5 to 9% of hydroxypropyl, 18 to 22% of methoxy and 27 to 35% of phthalic acid, with a molecular weight of 78,000 Daltons.

The enteric coating of the present disclosure is prepared by spraying an enteric coating solution onto a core through conventional methods. Solvents for the enteric coating are alcohols (such as ethanol), ketones (such as acetone), halogenated hydrocarbon compounds (such as dichloromethane) or a combination thereof. Softeners such as di-n-butyl phthalate and glyceryl triacetate are added to the enteric coating solution in a ratio of 1 part of the coating to about 0.05 parts (or about 0.3 parts) of the softener. The spraying method is preferably performed continuously, and the amount of spray material can be controlled according to the conditions for coating. The spray pressure can be adjusted flexibly, generally an average pressure of 1 to 1.5 Pa will generate ideal results.

The "pharmaceutically effective amount" or "safe and effective amount" in the specification refers to an amount which is functional or active to human and/or animals and is acceptable to human and/or animals. For example, a preparation containing $1\times10$-$1\times10^{15}$ cfu/ml or cfu/g (particularly $1\times10^4$-$1\times10^{10}$ cfu/ml or cfu/g, more particularly $1\times10^6$-$1\times10$ cfu/ml or cfu/g) of *Anaerofustis stercorihominis* and/or metabolites thereof can be prepared in the present disclosure.

When the *Anaerofustis stercorihominis* is used in the manufacture of a pharmaceutical composition, the effective dosage of *Anaerofustis stercorihominis* or metabolites thereof used may vary depending on the administration route and the severity of disease to be treated. A dosage form suitable for internal administration includes about $1\times10$-$1\times10^{15}$ cfu/ml or cfu/g (preferably $1\times10^4$-$1\times10^{10}$ cfu/ml or cfu/g, more preferably $1\times10^6$-$1\times10^{10}$ cfu/ml or cfu/g) of active *Anaerofustis stercorihominis* or its active component produced by fermentation, which is closely mixed with a solid or liquid pharmaceutically acceptable carrier. This dosage regimen can be adjusted to provide the best therapeutic response. For example, several divided doses may be administered daily or the dosage may be proportionally reduced according to the urgent need of treatment condition.

The *Anaerofustis stercorihominis* or metabolites thereof may be administered by oral route or the like. Solid carriers include starch, lactose, dicalcium phosphate, microcrystalline cellulose, sucrose and white clay; and liquid carriers include culture medium, polyethylene glycol, non-ionic surfactants and edible oils (such as corn oil, peanut oil and sesame oil), as long as they are suitable for the property of *Anaerofustis stercorihominis* or metabolites thereof and the specific administration means required. Adjuvants commonly used in the manufacture of a pharmaceutical composition may also be advantageously included, for example, flavoring agents, pigments, preservatives and antioxidants such as Vitamin E, Vitamin C, BHT and BHA.

From the standpoint of ease of manufacture and administration, the preferred pharmaceutical composition is a solid composition, especially tablets and/or solid-filled or liquid-filled capsules. Preferred is oral administration.

The composition of the present disclosure is administered to individuals (a subject, an experimental subject) once or several times per day. The dosage unit of administration refers to a dosage that can be physically separated and suitable for application in human or all individuals of other mammals. Each unit contains a pharmaceutically acceptable carrier and a therapeutically effective amount of microorganism of the present disclosure. The administration dosage varies with the body weight of patient and the severity of metabolic disease (such as obesity, diabetes, atherosclerosis-related diseases, cardiovascular disease), the contained supplementary active components and the microorganism used. Further, if possible, the composition can be administered separately and continuously as necessary. Therefore, the administration dosage does not limit the scope of the present disclosure. In addition, the "composition" in the present disclosure means not only a medicament but also a functional food and a health supplement food. In a preferred embodiment, the composition includes beverage, food, medicine, animal feed or the like.

In a preferred embodiment, the present disclosure further provides a food composition, which contains an effective amount of *Anaerofustis stercorihominis* and/or metabolites thereof as well as a food acceptable carrier as balance. The dosage form of the food composition is selected from a solid product, a dairy product, a solution product, a powder product or a suspension product. In a preferred embodiment, the food composition may further contain a growth factor, such as a milk growth factor. In a preferred embodiment, the composition further contains probiotics selected from the group consisting of Lactic acid bacteria, *Bifidobacteria*, *Lactobacillus acidophilus* or a combination thereof, and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Anaerofustis stercorihominis* (such as a protective agent), including cysteine, glutathione, butyl hydroxyanisole, dibutylmethyltoluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof.

In a preferred embodiment, the composition has the following formula:

$1\times10$-$1\times10^{15}$ cfu/mL of *Anaerofustis stercorihominis* and/or metabolites thereof; and a food acceptable or pharmaceutically acceptable carrier and/or excipient.

In another preferred embodiment, the composition has the following formula:

$1\times10^4$-$1\times10^{10}$ cfu/mL of *Anaerofustis stercorihominis* and/or metabolites thereof; and a food acceptable or pharmaceutically acceptable carrier and/or excipient.

Microecological Preparation

Microecological preparation is a biological preparation containing probiotics and metabolites thereof or a dietary supplement that can supply probiotics, which are capable of adjusting and maintaining the microecological balance in intestine, thus achieving the purpose of improving human health. The microecological preparation mainly includes probiotics, prebiotics and synbiotics.

In the present disclosure, the microecological preparation contains (a) a safe and effective amount of *Anaerofustis stercorihominis* and/or metabolites thereof, and (b) a food acceptable or pharmaceutically acceptable carrier. In a preferred embodiment, the preparation further contains a growth factor, such as a milk growth factor, preferably including vitamins, purines and/or pyrimidines. In a preferred embodiment, the preparation further contains probiotics selected from the group consisting of Lactic acid bacteria, *Bifidobacteria*, *Lactobacillus acidophilus* or a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Anaerofustis stercorihominis* (such as a protective agent) selected from the group consisting of cysteine, glutathione, butyl hydroxyanisole, dibutylmethyltoluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof.

Method for Producing *Anaerofustis stercorihominis*

Generally, *Anaerofustis stercorihominis* can be produced by conventional methods. In the present disclosure, provided is a method capable of producing *Anaerofustis stercorihominis* on a large scale. In particular, the method includes steps of:

(a) culturing the *Anaerofustis stercorihominis* of the present disclosure under a condition suitable for culturing, thereby obtaining a culture product;

(b) optionally, isolating *Anaerofustis stercorihominis* bacterial cells and/or metabolites thereof from the culture product; and (c) optionally, mixing the culture product obtained in (a) or the *Anaerofustis stercorihominis* bacterial cells and/or metabolites thereof obtained in (b) with a food acceptable or pharmaceutically acceptable carrier, thereby obtaining a composition.

In the present disclosure, the condition suitable for culturing refers to any conditions suitable for culturing *Anaerofustis stercorihominis* of the present disclosure. In a preferred embodiment, the condition suitable for culturing refers to anaerobic culturing with PYG medium at 37° C. for 24 to 72 hours.

Method of Reducing a Blood Glucose Level in Mammals

In a preferred embodiment, the method of reducing a blood glucose level in mammals includes: administering the *Anaerofustis stercorihominis*, the pharmaceutical composition, the food composition, the beverage composition or a combination thereof of the present disclosure to a subject. The subject includes mammals, such as human.

In a preferred embodiment, the method of reducing a blood glucose level in mammals includes: administering the *Anaerofustis stercorihominis*, the pharmaceutical composition, the food composition, the animal feed or a combination thereof of the present disclosure to a subject. The subject includes animals, preferably a murine or a rabbit.

Method of Ameliorating Glucose Intolerance in Mammals

In a preferred embodiment, the method of ameliorating glucose intolerance in mammals includes: administering the *Anaerofustis stercorihominis*, the pharmaceutical composition, the food composition, the beverage composition or a combination thereof of the present disclosure to a subject. The subject includes mammals, such as human.

In a preferred embodiment, the method of ameliorating glucose intolerance in mammals includes: administering the *Anaerofustis stercorihominis*, the pharmaceutical composition, the food composition, the animal feed or a combination thereof of the present disclosure to a subject. The subject includes animals, preferably a murine or a rabbit.

Method of Ameliorating Myocardial Ischemia in Mammals

In a preferred embodiment, the method of ameliorating myocardial ischemia in mammals includes: administering the *Anaerofustis stercorihominis*, the pharmaceutical composition, the food composition, the beverage composition or a combination thereof of the present disclosure to a subject. The subject includes mammals, such as human.

In a preferred embodiment, the method of ameliorating myocardial ischemia in mammals includes: administering the *Anaerofustis stercorihominis*, the pharmaceutical composition, the food composition, the animal feed or a combination thereof of the present disclosure to a subject. The subject includes animals, preferably a murine or a rabbit.

Method of Reducing a Blood Lipid Level in Mammals

In a preferred embodiment, the method of reducing a blood lipid level in mammals includes: administering the *Anaerofustis stercorihominis*, the pharmaceutical composition, the food composition, the beverage composition or a combination thereof of the present disclosure to a subject. The subject includes mammals, such as human.

In a preferred embodiment, the method of reducing a blood lipid level in mammals includes: administering the *Anaerofustis stercorihominis*, the pharmaceutical composition, the food composition, the animal feed or a combination thereof of the present disclosure to a subject. The subject includes animals, preferably a murine or a rabbit.

Method of Reducing Body Weight of Mammals

In a preferred embodiment, the method of reducing body weight of mammals includes: administering the *Anaerofustis*

*stercorihominis*, the pharmaceutical composition, the food composition, the beverage composition or a combination thereof of the present disclosure to a subject. The subject includes mammals, such as human.

In a preferred embodiment, the method of reducing body weight of mammals includes: administering the *Anaerofustis stercorihominis*, the pharmaceutical composition, the food composition, the animal feed or a combination thereof of the present disclosure to a subject. The subject includes animals, preferably a murine or a rabbit.

Method of Ameliorating Vasculopathy in Mammals

In a preferred embodiment, the method of ameliorating vasculopathy in mammals includes: administering the *Anaerofustis stercorihominis*, the pharmaceutical composition, the food composition, the beverage composition or a combination thereof of the present disclosure to a subject. The subject includes mammals, such as human.

In a preferred embodiment, the method of ameliorating vasculopathy in mammals includes: administering the *Anaerofustis stercorihominis*, the pharmaceutical composition, the food composition, the animal feed or a combination thereof of the present disclosure to a subject. The subject includes animals, preferably a murine or a rabbit.

Method of Preventing and/or Treating Metabolic Diseases

In a preferred embodiment, the method of preventing and/or treating metabolic diseases includes: administering the *Anaerofustis stercorihominis*, the pharmaceutical composition, the food composition, the beverage composition or a combination thereof of the present disclosure to a subject. The subject includes mammals, such as human.

In a preferred embodiment, the method of preventing and/or treating metabolic diseases includes: administering the *Anaerofustis stercorihominis*, the pharmaceutical composition, the food composition, the animal feed or a combination thereof of the present disclosure to a subject. The subject includes animals, preferably a murine or a rabbit.

Deposit of Microorganism

The strain *Anaerofustis stercorihominis* AM25-6 of the present disclosure was deposited at Guangdong Microbial Culture Collection Center (GDMCC, fifth floor of No. 59 Building, 100 Xianlie Middle Road, Guangzhou) on Oct. 13, 2016, with a deposit number of GDMCC 60087 and a deposit name of *Anaerofustis stercorihominis* AM25-6.

The present disclosure mainly has the following advantages:
- the *Anaerofustis stercorihominis* of the present disclosure can significantly treat and/or prevent lipid metabolism related diseases, such as obesity, diabetes, atherosclerosis-related diseases, cardiovascular disease or the like.
- (b) the *Anaerofustis stercorihominis* of the present disclosure can significantly reduce body weight and blood lipids, such as lowering levels of total cholesterol, triglyceride, low-density lipoprotein and blood viscosity.
- (c) the *Anaerofustis stercorihominis* of the present disclosure can significantly ameliorate myocardial ischemia and vasculopathy.
- (d) the *Anaerofustis stercorihominis* of the present disclosure can significantly reduce blood glucose and ameliorate glucose intolerance in mammals.
- (e) the *Anaerofustis stercorihominis* of the present disclosure exhibits significant efficacy, nearly without toxic and side effects, thus greatly reducing the treatment cost.

The present disclosure is further described as below with reference to specific embodiments. It should be understood that these examples are only for illustrating the present disclosure and not intended to limit the scope of the present disclosure. The conditions of experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions.

Unless otherwise specified, the materials and agents used in the examples are all commercially available products.

EXAMPLE 1

Isolation and Identification of *Anaerofustis stercorihominis* AM25-6

1.1 Isolation of AM25-6

The sample to be isolated was obtained from faeces of a healthy male, which was collected via a sterile sample tube and brought back to the laboratory for sorting within 1 hour. The obtained fresh samples were immediately transferred to an anaerobic operation box, and 0.2 g of the sample was suspended in 1 ml of sterile phosphate buffered saline (PBS), shaken and mixed thoroughly. The isolation of strain was conducted by a spread plate method in gradient dilution. The plates were cultured by PYG medium (purchased from Huankai Microbial Technology Co., Ltd.) in an anaerobic condition (anaerobic gas components: $N_2$: $CO_2$: $H_2$=90: 5: 5) at 37° C. for 3 days. Single colonies were picked out and purified by streaking to obtain a pure culture of each single colony. The purely cultured strains obtained were further cultured to a concentration of about $10^9$ cfu/ml, and 400 μl of bacterial liquid was added with 400 μl of 40% glycerol to make the glycerol concentration to 20%, followed by cryopreservation at −80° C.

1.2 Identification of 16S rDNA

The genomic DNA of isolated bacteria was extracted, followed by PCR amplification using 16S rDNA universal primer 27f (5'-AGAGTTTGATCATGGCTCAG-3', SEQ ID NO.: 2) and primer 1492r (5'-TAGGGTTACCTTGT-TACGACTT-3', SEQ ID NO.:3). The amplification system is 3 μl of 10×PCR buffer, 2.5 μl of dNTP, 0.5 μl of primer 27F, 0.5 μl of primer 1492R, 0.3 μl of Taq polymerase, 1 μl of genomic template, and 18.2 μl of dd$H_2$O. The amplification condition was as below: pre-degeneration at 95° C. for 4 minutes; 30 cycles for 95° C. 30 s, 57° C. 40 s and 72° C. 90 s.

The obtained 16S rDNA amplification product was subjected to electrophoretic detection, purification and 3730 sequencing to obtain a 16S rDNA sequence (SEQ ID NO.:1) of a length of 1425 bp. The 16S rDNA sequence of strain AM25-6 was subjected to alignment based on EzBioCloud database (http://www.ezbiocloud.net/identify). It is found that strain *Anaerofustis stercorihominis* DSM 17244 (purchased from the Deutsche Sammlung von Mikroorganismen und Zellkulturen, DSMZ) has the highest homology (i.e., 99.86%) with the AM25-6.

1.3 Physiological and Biochemical Characteristics of AM25-6

The colony characteristics of *Anaerofustis stercorihominis* AM25-6 after culturing for 72 hours in PYG medium is light yellow, needle-shaped and small size, with a diameter of about 0.2 mm. The mycelium under microscope is short rod-shaped, Gram-positive, and does not produce spores and flagella according to Gram staining and spore flagella staining. *Anaerofustis stercorihominis* AM25-6 is detected to be negative to both catalase and oxidase. The AM25-6 on carbon source utilization was detected by API 20A (Mérieux, France), with results shown in Table 1, in which "+" indicates a positive reaction, "−" indicates a negative reaction and "w" indicates a weak positive reaction.

TABLE 1

| Nos. | Reaction | Result |
|---|---|---|
| 1 | production of indole | − |
| 2 | urea (urease) | − |
| 3 | glucose | + |
| 4 | mannitol | w |
| 5 | lactose | + |
| 6 | sucrose | + |
| 7 | maltose | + |
| 8 | salicyl alcohol | w |
| 9 | xylose | w |
| 10 | arabinose | − |
| 11 | Gelatin hydrolysis | + |
| 12 | esculin | − |
| 13 | glycerin | − |
| 14 | cellobiose | − |
| 15 | mannose | + |
| 16 | melezitose | w |
| 17 | raffinose | w |
| 18 | sorbitol | w |
| 19 | rhamnose | w |
| 20 | trehalose | + |

1.4 Antibiotic Sensitivity of AM25-6

The sensitivity of AM25-6 to 20 common antibiotics was tested by the drug sensitive paper method. 100 µl of AM25-6 bacterial solution cultured to the logarithmic phase was spread plated. Antibiotic susceptibility papers (purchased from Hangzhou Microbial Reagent Co. LTD) were affixed on the medium surface of plates, cultured at 37° C. for 48 hours, after which the size of inhibition zone was measured. The results are shown in Table 2.

TABLE 2

| Antibiotics | Diameter of inhibition zone (cm) |
|---|---|
| Penicillin | 3.0 |
| Oxacillin | 1.0 |
| Ampicillin | >4.0 |
| Carbenicillin | >4.0 |
| Kanamycin | 1.8 |
| Cefalexin | 2.0 |
| Cefazolin | 2.6 |
| Cefradine | 2.0 |
| Piperacillin | 3.0 |
| Cefuroxime | 3.0 |
| Ceftriaxone Sodium | >4.0 |

TABLE 2-continued

| Antibiotics | Diameter of inhibition zone (cm) |
|---|---|
| Cefoperazone | >4.0 |
| Amikacin Δ | 1.5 |
| Gentamicin | 2.0 |
| Fortum (Ceftazidime) Δ | >4.0 |
| Neomycin | 1.0 |
| Tetracycline | 0.9 |
| Doxycycline | 2.0 |
| Minocin (Minocycline) Δ | 2.6 |
| Erythromycin | 2.0 |

The results show that the AM25-6 is sensitive to all of the 20 common antibiotics, thus the strain has a high safety.

EXAMPLE 2

Bioactive Components of *Anaerofustis stercorihominis* AM25-6

This example mainly examined the generation of metabolites of AM25-6 after culturing in PYG culture for 48 hours, mainly including the content of short-chain fatty acids (SCFAs) and organic acids. SCFAs mainly include acetic acid, propionic acid, butyric acid and valeric acid. Organic acids include 3-methyl butyric acid, quinic acid, lactic acid, oxalic acid, malonic acid, benzoic acid, maleic acid, succinic acid, trans-fumaric acid, malic acid, adipic acid, tartaric acid, shikimic acid, citric acid, isocitric acid and L-ascorbic acid. The standards of each SCFAs and organic acids are purchased from Sigma. The detection procedure is as follows.

2.1 Sample Pretreatment 1 ml of AM25-6 bacterial solution was taken for centrifugation at 12000 r/min for 5 minutes, and the supernatant was collected for detection of short-chain fatty acids (SCFAs) and organic acids.

2.2 Determination of SCFAs

The SCFAs were detected by using the gas chromatograph of Agilent (GC-7890B, Agilent), in which the capillary column (30 m×0.25 mm×0.25 µm) from HP-INNOWax (Cross-Linked PEG) was selected for analysis, and the detector was a hydrogen flame ion detector.

The parameters of the GC were set as follows: column temperature of 180~200° C.; gasification chamber temperature of 240° C.; detection temperature of 210° C.; injection volume of 2 µl; flow rate of carrier gas: $N_2$, 50 ml/min; hydrogen flow rate of 50 ml/min; and air flow rate of 600~700 ml/min.

2.3 Determination of Organic Acids

The organic acids were also detected by the gas chromatograph of Agilent (GC-7890B, Agilent). 122-5532G DB-5 ms column (40 m×0.25 mm×0.25 µm) is used, in which column temperature is 270~290° C., inlet temperature is 250° C. and gas flow rate is 0.86 ml/min. 2.4 Experimental Results

TABLE 3

| Products | acetic acid | formic acid | propionic acid | iso-butyric acid | butyric acid |
|---|---|---|---|---|---|
| Content (mmol/L) | 4.53 | 0 | 0 | 0.35 | 1.56 |
| Products | isovaleric acid | valeric acid | benzoic acid | 3-methyl butyric acid | quinic acid |
| Content (mmol/L) | 1.11 | 0.78 | 4.66 | 0.39 | 0 |

TABLE 3-continued

| Products | lactic acid | oxalic acid | malonic acid | benzoic acid | maleic acid |
|---|---|---|---|---|---|
| Content (mmol/L) | 4.97 | 0 | 0 | 0.04 | 0 |
| Products | succinic acid | trans-fumaric acid | malic acid | adipic acid | tartaric acid |
| Content (mmol/L) | 0.42 | 0 | 0 | 0.06 | 0 |
| Products | shikimic acid | citric acid | D, L-isocitric acid trisodium salt | L-Vitamin C | |
| Content (mmol/L) | 0 | 0.19 | 0 | 0 | |

The results in Table 3 show that the AM25-6 is capable of producing acetic acid, butyric acid, isovaleric acid, benzoic acid and lactic acid, and can also produce a small amount of isobutyric acid, valeric acid, 3-methyl butyric acid, succinic acid, adipic acid and citric acid.

The information of stains used in the following examples is described as follows.

The *Anaerofustis stercorihominis* AM25-6, DSM 17244, DSM 28733 were cultured by using PYG medium in an anaerobic condition at 37° C. The colony of *Anaerofustis stercorihominis* AM25-6 after culturing for 2 days in PYG medium is light yellow, needle-shaped and small size, with a diameter of about 0.5 mm. The mycelium under microscope is short rod-shaped, Gram-positive, and does not produce spores and flagella.

The strain *Anaerofustis stercorihominis* AM25-6 of the present disclosure was deposited at Guangdong Microbial Culture Collection Center (GDMCC, fifth floor of No. 59 Building, 100 Xianlie Middle Road, Guangzhou) on Oct. 13, 2016, with a deposit number of GDMCC 60087 and a deposit name of *Anaerofustis stercorihominis* AM25-6.

The strain *Anaerofustis stercorihominis* DSM 17244 of the present disclosure was purchased from the Deutsche Sammlung von Mikroorganismen und Zellkulturen (DSMZ).

The strain *Anaerofustis stercorihominis* DSM 28733 of the present disclosure was purchased from the Deutsche Sammlung von Mikroorganismen und Zellkulturen (DSMZ).

TABLE 4

Strain information

| Nos. | Name of strain |
|---|---|
| Bacterial agent 1 | *Anaerofustis stercorihominis* AM25-6 |
| Bacterial agent 2 | *Anaerofustis stercorihominis* DSM 17244 |
| Bacterial agent 3 | *Anaerofustis stercorihominis* DSM 28733 |

EXAMPLE 3

Efficacy of *Anaerofustis stercorihominis* in an Obesity Animal Model

The obesity animal model is constructed by using C57BL/6 male mice (purchased from Guangdong Medical Experimental Animal Center) at 8 weeks old and 20±2 g of body weight, which is housed in a specific pathogen free (SPF) environment and access to food and water ad lib. The mice are randomly divided into 5 groups, with 10 mice in each group.

Control group: mice were fed with ordinary maintenance feed every day;

Bacterial agent group 1: mice were fed with high-fat feed every day, in which the AM25-6 bacterial solution ($1 \times 10^8$ cfu/ml) was administered by gavage for 9 weeks after 4 weeks of feeding high-fat feed;

Bacterial agent group 2: mice were fed with high-fat feed every day, in which the DSM 17244 bacterial solution ($1 \times 10^8$ cfu/ml) was administered by gavage for 9 weeks after 4 weeks of feeding high-fat feed;

Bacterial agent group 3: mice were fed with high-fat feed every day, in which the DSM 28733 bacterial solution ($1 \times 10^8$ cfu/ml) was administered by gavage for 9 weeks after 4 weeks of feeding high-fat feed;

Obesity model group: mice were fed with high-fat feed every day, in which the culture medium in a same amount was administered by gavage for 9 weeks after 4 weeks of feeding high-fat feed.

During the experimental period, experimental data such as the body weight, body condition and food intake amount of mice were recorded every week. After the completion of experiment, the mice were sacrificed, and the fat weight was recorded and the serum was collected for detecting blood lipids by using the Elisa kit.

TABLE 5

Weight gain of mice in each group before and after administration of *Anaerofustis stercorihominis* by gavage

| Groups | Week 1 (g) | Week 3 (g) | Week 5 (g) | Week 7 (g) | Week 9 (g) |
|---|---|---|---|---|---|
| Control group | 20.35 | 21.21 | 21.68 | 22.77 | 23.78 |
| Bacterial agent group 1 | 21.13 | 22.59 | 23.98 | 24.13 | 25.47* |
| Bacterial agent group 2 | 20.15 | 21.78 | 22.99 | 23.88 | 25.62* |
| Bacterial agent group 3 | 21.19 | 22.44 | 23.78 | 24.19 | 25.67* |
| Obesity model group | 22.49 | 24.92 | 26.49 | 27.65 | 29.46 |

The results show that the body weight of mice increases gradually as the experiment progresses, in which the administration of *Anaerofustis stercorihominis* by gavage after feeding with high-fat feed can significantly control the weight gain rate of mice through the results of the obesity model group and *Anaerofustis stercorihominis* bacterial agent groups 1, 2 and 3, indicating *Anaerofustis stercorihominis* can effectively slow down the weight gain of obesity mice model (relative to model group, *$P<0.05$).

EXAMPLE 4

Efficacy of *Anaerofustis stercorihominis* in a Diabetes Animal Model

The T2D animal model is constructed by using C57bL/6 mice (purchased from Guangdong Medical Experimental Animal Center) at 8 weeks old and 20±2 g of body weight. The mice were housed in a specific pathogen free (SPF) environment and adaptively fed for 1 week, followed by grouping and modeling. The T2D animal model is induced by injection of streptozotocin (STZ) along with feeding high-fat feed, and the mice having fasting blood glucose (FBG) reaching to 10 mM/L can be used as a T2D mice model. Fifty mice selected for experiments are randomly divided into 5 groups.

Model group: the T2D mice model was administered with saline solution by gavage;

Bacterial agent group 1: the T2D mice model was administered with the AM25-6 bacterial solution ($1\times10^8$ cfu/ml) by gavage;

Bacterial agent group 2: the T2D mice model was administered with the DSM 17244 bacterial solution ($1\times10^8$ cfu/ml) by gavage;

Bacterial agent group 3: the T2D mice model was administered with the DSM 28733 bacterial solution ($1\times10^8$ cfu/ml) by gavage;

Metformin treatment group: the T2D mice model was treated with the positive drug metformin.

The experiment was carried out based on the different groups. After the construction of T2D mice model (i.e., FBG>10), the treatment was started and lasted for 2 months. The food intake amount and body weight of mice were recorded daily. Blood of mice was collected from the tail vein every week for detection of fasting blood glucose. The oral glucose tolerance test (OGTT) of mice was measured at week 4 of treatment and at the end of the experiment.

TABLE 6

Table of weight change

| Groups | Week 1 (g) | Week 3 (g) | Week 5 (g) | Week 7 (g) | Week 9 (g) |
|---|---|---|---|---|---|
| Model group | 21.86 | 23.65 | 27.92 | 29.35 | 31.12 |
| Bacterial agent group 1 | 22.34 | 23.57 | 24.26 | 25.53 | 25.97* |
| Bacterial agent group 2 | 21.55 | 22.43 | 23.78 | 25.13 | 25.58* |
| Bacterial agent group 3 | 21.76 | 23.36 | 24.57 | 25.14 | 25.45* |
| Metformin treatment group | 20.33 | 22.36 | 24.63 | 25.86 | 26.53* |

The results show that the body weight of mice increases gradually as the experiment progresses, in which the weight gain of mice in the *Anaerofustis stercorihominis* bacterial agent groups 1, 2 and 3 as well as the metformin treatment group is lower than that of mice in the model group, indicating that *Anaerofustis stercorihominis* can effectively slow down the weight gain of T2D mice model (relative to model group, *P<0.05/**P<0.01). Meanwhile, *Anaerofustis stercorihominis* has a more effective efficacy on controlling weight gain of T2D mice than the metformin.

TABLE 7

Experimental results of effect of *Anaerofustis stercorihominis* on fasting blood glucose in mice model

| Groups | Week 1 (mmol/L) | Week 3 (mmol/L) | Week 5 (mmol/L) | Week 7 (mmol/L) | Week 9 (mmol/L) |
|---|---|---|---|---|---|
| Model group | 15.9 | 17.1 | 17.9 | 17.4 | 16.2 |
| Bacterial agent group 1 | 16.1 | 15.6 | 13.2* | 10.4** | 8.6** |
| Bacterial agent group 2 | 15.8 | 15.7 | 14.6 | 11.7* | 9.0** |
| Bacterial agent group 3 | 16.7 | 15.5 | 13.6* | 10.4** | 7.8** |
| Metformin treatment group | 16.8 | 16.2 | 13.9 | 11.5* | 10.1** |

The results show that the fasting blood glucose level of mice in the *Anaerofustis stercorihominis* bacterial agent groups 1, 2 and 3 as well as the metformin treatment group gradually decreases as the treatment progresses, thus the blood glucose level of the mice tends to be normal, with significant hypoglycemic effect. This indicates that the *Anaerofustis stercorihominis* bacterial agent groups 1, 2 and 3 can effectively reduce blood glucose compared to the model group (*P value<0.05/**P<0.01). Meanwhile, the fasting blood glucose level of mice in the *Anaerofustis stercorihominis* bacterial agent groups 1, 2 and 3 is lower than that of mice in the metformin treatment group, indicating that *Anaerofustis stercorihominis* has a better efficacy on decreasing fasting blood glucose than metformin.

TABLE 8

Effect of *Anaerofustis stercorihominis* on glucose tolerance in mice model

| Groups | 0 minute | 30 minutes | 60 minutes | 90 minutes | 120 minutes |
|---|---|---|---|---|---|
| Model group | 15.6 | 23.1 | 17.1 | 16.2 | 15.1 |
| Bacterial agent group 1 | 9.1 | 17.8 | 15.9 | 11.5* | 10.1* |
| Bacterial agent group 2 | 9.7 | 18.0 | 14.9 | 12.1* | 9.9* |
| Bacterial agent group 3 | 9.6 | 18.2 | 15.6 | 11.7* | 10.2* |
| Metformin treatment group | 9.3 | 18.6 | 16.4 | 11.7* | 10.3* |

The results of oral glucose tolerance test (OGTT) for mice shown in Table 8 indicate that the blood glucose of mice reaches the highest level (i.e., 17.8-23.1 mmol/L) at 30 minutes upon administration of glucose by gavage. The blood glucose level of mice in the *Anaerofustis stercorihominis* bacterial agent groups 1, 2 and 3 uniformly decreased and reached to 10.1 mmol/L, 9.9 mmol/L, 10.2 mmol/L respectively as well the metformin treatment group uniformly decreased and reached to 10.3 mmol/L at 120 minutes, whereas the blood glucose of mice in the model group is 15.1 mmol/L at 120 minutes, meaning that the blood glucose level is significantly different between the *Anaerofustis stercorihominis* bacterial agent groups 1, 2, 3 and the metformin treatment group (*P value<0.05). From the perspective of overall glucose tolerance process, it can be seen that *Anaerofustis stercorihominis* can effectively ameliorate glucose intolerance in diabetic mice. Throughout the process of regulating glucose, the *Anaerofustis stercorihominis* bacterial agent groups 1, 2, 3 showed a lower blood glucose level than the metformin treatment group at each time point, indicating that *Anaerofustis stercorihominis* has a better efficacy on ameliorating glucose intolerance in diabetic mice than metformin.

EXAMPLE 5

Efficacy of *Anaerofustis stercorihominis* in a Hyperlipidemia Animal Model

Sixty C57bL/6 mice (purchased from Guangdong Medical Experimental Animal Center) at 6 weeks old were used in this experiment, which were normally fed in a Specific pathogen Free (SPF) environment. The mice were adaptively fed for 1 week and then randomly divided into 6 groups, with 10 mice in each group. The animal model is constructed along with intervention.

Model control group: the mice were fed with high-fat feed and 2 ml of phosphate buffered saline (PBS) daily;

Bacterial agent group 1: the mice were fed with high-fat feed and 2 ml of AM25-6 bacterial solution ($1\times10^9$ cfu/ml) daily;

Bacterial agent group 2: the mice were fed with high-fat feed and 2 ml of DSM 17244 bacterial solution ($1\times10^9$ cfu/ml) daily;

Bacterial agent group 3: the mice were fed with high-fat feed and 2 ml of DSM 28733 bacterial solution ($1\times10^9$ cfu/ml) daily;

Tongmai Jiangzhi tablet group (a positive drug for the treatment of hyperlipidemia): the mice were fed with high-fat feed and 0.6 g/kg Tongmai Jiangzhi tablets;

Normal control group: the mice were fed with ordinary feed.

Experimental data such as the body condition, food intake amount and the like of mice was recorded every week before and after the intervention of the model. After the completion of experiment, the mice were sacrificed, and the fat content was recorded, the serum was collected for detection of blood lipid contents (including total cholesterol (TC), triglyceride (TG), high-density lipoprotein (HDLC) and low-density lipoprotein (LDLC)) in the serum according to the instruction of kit. Blood from the last carotid artery was taken for hemorheological examination.

TABLE 9

Experimental results of effect of *Anaerofustis stercorihominis* AM25-6 on blood lipids in mice

| Groups | TC (total cholesterol) (mmol/L) | TG (tri-glyceride) (mmol/L) | LDLC (low-density lipo-protein) (mmol/L) | HDLC (high-density lipo-protein) mmol/L) | blood vis-cosity |
|---|---|---|---|---|---|
| Model control group | 4.643 | 1.235 | 2.658 | 3.319 | 2.35 |
| Tongmai Jiangzhi tablet group | 4.032 | 0.947 | 1.644 | 3.212 | 1.34 |
| Bacterial agent group 1 | 4.014* | 0.893* | 1.454* | 3.219 | 1.26* |
| Bacterial agent group 2 | 4.021* | 0.933* | 1.585* | 3.219 | 1.29* |
| Bacterial agent group 3 | 4.017* | 0.912* | 1.423* | 3.311 | 1.25* |
| Normal control group | 3.432 | 0.849 | 1.457 | 3.260 | 1.02 |

The results show that the main components of blood lipid are cholesterol and triglyceride, in which the increase of cholesterol and triglyceride levels in plasma is closely related to the onset of atherosclerosis. It can be seen from Table 9 that the intervention of *Anaerofustis stercorihominis* can effectively control the levels of TC, TG, LDLC in blood and blood viscosity relative to the model control group (*$P<0.05$), achieving a similar efficacy to that of Tongmai Jiangzhi tablet, indicating that *Anaerofustis stercorihominis* can indeed reduce blood lipids and indicators related to atherosclerosis-related diseases and cardiovascular disease, as well as significantly reduce blood viscosity, thereby effectively preventing the blood from being a state of high viscosity and high coagulation, thus ameliorating hemorheology and relieving vascular disease.

EXAMPLE 6

Efficacy of *Anaerofustis stercorihominis* on Experimental Myocardial Ischemia in Rats Fifty SD rats (purchased from Guangdong Medical Experimental Animal Center, half male and half female) at 180-220 g of body weight and 6 weeks old were used in this experiment, which were normally fed in a Specific pathogen Free (SPF) environment. The rats were adaptively fed for 1 week and then randomly divided into 5 groups, with 10 rats in each group.

Model group: the rats were fed with 2.5 ml/kg PBS by gavage daily for 10 consecutive days; Bacterial agent group 1: the rats were fed with 2.5 ml/kg AM25-6 bacterial solution ($1\times10^9$ cfu/ml) by gavage daily for 10 consecutive days;

Bacterial agent group 2: the rats were fed with 2.5 ml/kg DSM 17244 bacterial solution ($1\times10^9$ cfu/ml) by gavage daily for 10 consecutive days;

Bacterial agent group 3: the rats were fed with 2.5 ml/kg DSM 28733 bacterial solution ($1\times10^9$ cfu/ml) by gavage daily for 10 consecutive days;

FuFangDanShen tablet group: the rats were fed with 2 g/kg FuFangDanShen tablet (SFDA approval number Z21020381, Tianjin Tasly (Liaoning) Pharmaceutical Co., Ltd.) by gavage daily for 10 consecutive days.

For each group, the standard lead I electrocardiogram was recorded post 1 hour of last administration, followed by sublingual intravenous injection (iv.) with pituitrin (SFDA approval number H31022259, specifications: 2 ml: 6 units, from Shanghai First Biochemical & Pharmaceutical Industry Co., Ltd.) in 1 unit/kg (in a volume of 1 ml/kg) within 15 seconds, after which the change of electrocardiogram was recorded post 5 seconds, 15 seconds, 30 seconds, 1 minute, 2 minutes, 3 minutes and 5 minutes, and the change of ST segment displacement before and after administration of pituitrin was measured and compared, with statistical analysis by using t test between groups. The specific experimental results are shown in Table 10.

TABLE 10

Effect of bacterial agent and Danshen tablet on ST-segment displacement of rat myocardial ischemia induced by pituitrin

| Groups | ST-segment displacement (mv) (±S) |
|---|---|
| Model group | 0.060 ± 0.013 |
| FuFangDanShen tablet group | 0.033 ± 0.015* |
| Bacterial agent group 1 | 0.017 ± 0.011** |
| Bacterial agent group 2 | 0.018 ± 0.012** |
| Bacterial agent group 3 | 0.020 ± 0.012** |

According to the statistics in Table 10, the *Anaerofustis stercorihominis* provided in the present disclosure can effectively reduce the ST segment displacement of myocardial ischemia in rats relative to the model group (**$P<0.01$, *$P<0.05$), indicating that the bacterial agents provided in the present disclosure have an excellent relieving and protective effect on myocardial ischemia, and the effect of which is superior than that of the FuFangDanShen tablet group.

EXAMPLE 7

Food Composition Containing *Anaerofustis stercorihominis* AM25-6

Raw materials and proportion thereof were shown in Table 11.

TABLE 11

| Raw material(s) | Mass percentage (%) |
|---|---|
| *Anaerofustis stercorihominis* AM25-6 | 0.5 |
| milk | 90.0 |
| sugar | 9.0 |
| Vitamin C | 0.5 |

Milk and sugar in proportion of formula as above were mixed, stirred to complete mixture, preheated, homogenized at the pressure of 20 Mpa, and then sterilized at about 90° C. for 5 to10 mins, cooled to 40 to 43° C., followed by adding a protective agent (Vitamin C) and inoculation of $1\text{-}100\times10^6$ cfu/g *Anaerofustis stercorihominis* AM25-6, thus obtaining the food composition containing *Anaerofustis stercorihominis* AM25-6.

EXAMPLE 8

Pharmaceutical Composition Containing *Anaerofustis stercorihominis* AM25-6

Raw materials and proportion thereof were shown in Table 12.

TABLE 12

| Raw material(s) | Mass percentage (%) |
|---|---|
| *Anaerofustis stercorihominis* AM25-6 | 1.0% |
| lactose | 2.0% |
| yeast powder | 2.0% |
| peptone | 1.0% |
| purified water | 93.5% |
| vitamin C | 0.5% |

Lactose, yeast powder and peptone in proportion were mixed with purified water to be uniform, preheated to 60 to 65° C., homogenized at the pressure of 20 Mpa, and then sterilized at about 90° C. for 20 to 30 mins, cooled to 36 to 38° C., followed by adding vitamin C and inoculation of $1\text{-}50\times10^6$ cfu/mL active *Anaerofustis stercorihominis* AM25-6, after which fermented at 36 to 38° C. to pH 6.0, centrifuged, freeze-dried to less than 3% of water content, thus obtaining a freeze-dried product containing *Anaerofustis stercorihominis* AM25-6. 0.5 g of the freeze-dried product containing *Anaerofustis stercorihominis* AM25-6 was weighed, mixed with an equal amount of maltodextrin and a protective agent (such as vitamin C, cysteine), and then encapsulated into capsules, thus obtaining the pharmaceutical composition containing *Anaerofustis stercorihominis* AM25-6.

EXAMPLE 9

Method of Preparing a Medicine for the Treatment of Metabolic Diseases

1. Preparation of bacterial solution

*Anaerofustis stercorihominis* AM25-6 ($1\times10^9$ cfu/ml) were anaerobically fermented in the PYG medium at 37° C. for 2 to 3 days.

2. Preparation of growth factors

The skimmed milk and casein were mixed, centrifuged and ultra-filtered to obtain a crude extract of milk growth factor, including nutrients of vitamins, purines and/or pyrimidines.

3. Manufacture of a medicament or pharmaceutical dosage form 5 volumes (ml) of growth factor and 1 volume (ml) of protective agent (such as vitamin C, cysteine) were added to 100 volumes (ml) of the fermented bacterial solution of *Anaerofustis stercorihominis* AM25-6, fully stirred to be uniform, and then added with starch excipients (such as maltodextrin), thus obtaining the medicament or pharmaceutical dosage form containing *Anaerofustis stercorihominis* AM25-6.

The present disclosure is illustrated by specific examples as above, and these examples are only for understanding the present disclosure and do not limit the scope of the present disclosure. Several simple deductions, modifications or substitutions can be made by those skilled in the art according to the concept of the present disclosure.

What is claimed is:

1. A method for treating a metabolic disease, said method comprising:
   administering an *Anaerofustis stercorihominis* AM25-6 strain with a deposit number of GDMCC 60087 or a composition comprising the *Anaerofustis stercorihominis* AM25-6 strain with a deposit number of GDMCC 60087 to a subject in need thereof to treat the metabolic disease.

2. The method of claim 1, wherein the *Anaerofustis stercorihominis* AM25-6 strain with a deposit number of GDMCC 60087 comprises a 16s rDNA having the nucleotide sequence of SEQ ID NO: 1.

3. The method of claim 1, wherein the *Anaerofustis stercorihominis* AM25-6 strain with a deposit number of GDMCC 60087 or the composition is administered orally.

4. The method of claim 1, wherein the subject comprises a human or a non-human mammal.

5. The method of claim 1, wherein the metabolic disease comprises a lipid metabolism disease and an insulin metabolism disease.

6. The method of claim 1, wherein the composition comprises: (a) a safe and effective amount of *Anaerofustis stercorihominis* AM25-6 strain with a deposit number of GDMCC 60087, and (b) a food acceptable or pharmaceutically acceptable carrier.

7. The method of claim 1, wherein the composition comprises $1 \times 10^{-1}$ to $1 \times 10^{20}$ cfu/mL or cfu/g of *Anaerofustis stercorihominis* AM25-6 strain with a deposit number of GDMCC 60087 based on the total volume or total weight of the composition.

8. The method of claim 1, wherein the composition further comprises probiotics and/or prebiotics.

9. The method of claim 1, wherein the composition further comprises a substance capable of maintaining the vitality of *Anaerofustis stercorihominis* AM25-6 strain with a deposit number of GDMCC 60087.

10. The method of claim 1, wherein the composition is selected from the group consisting of a food composition, a health care composition, a pharmaceutical composition, a beverage composition, a feed composition, or a combination thereof.

11. The method of claim 1, wherein the *Anaerofustis stercorihominis* AM25-6 strain with a deposit number of GDMCC 60087 exhibits one or more activities selected from the group consisting of:
   (i) reducing a blood glucose level in mammals;
   (ii) ameliorating glucose intolerance in mammals;
   (iii) ameliorating myocardial ischemia in mammals;
   (iv) reducing a blood lipid level in mammals;
   (v) reducing body weight of mammals; and
   (vi) ameliorating vasculopathy in mammals.

12. The method of claim 1, wherein the composition is in a unit dosage form and the composition in each unit dosage form is of a mass of 0.05 g to 5 g.

13. The method of claim 8, wherein the probiotics are selected from the group consisting of Lactic acid bacteria, *Bifidobacteria*, *Lactobacillus acidophilus* or a combination thereof, and
   the prebiotics are selected from the group consisting of fructooligosaccharide (FOS), galactooligosaccharide (GOS), xylooligosaccharide (XOS), lactosucrose (LACT), soybean oligosaccharides (SOS), Inulin oligosaccharide or a combination thereof.

14. The method of to claim 1, wherein the administering step is in dosage of 0.01 to 5 g/50 kg body weight per day.

15. The method of claim 1, wherein the metabolic disease is selected from the group consisting of obesity, diabetes, atherosclerosis-related diseases, cardiovascular disease, or a combination thereof.

* * * * *